(12) United States Patent
Tan Hehir et al.

(10) Patent No.: US 8,114,382 B2
(45) Date of Patent: *Feb. 14, 2012

(54) MYELIN DETECTION USING BENZOFURAN DERIVATIVES

(75) Inventors: Cristina Abucay Tan Hehir, Niskayuna, NY (US); Stephen Johnson Lomnes, Philadelphia, PA (US); Kenneth Michael Fish, Clifton Park, NY (US); Tiberiu Mircea Siclovan, Rexford, NY (US); Michael Christopher Montalto, Albany, NY (US); Tunchiao Hubert Lam, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 720 days.

This patent is subject to a terminal disclaimer.

(21) Appl. No.: 12/211,854

(22) Filed: Sep. 17, 2008

(65) Prior Publication Data

US 2010/0068140 A1 Mar. 18, 2010
US 2011/0305635 A9 Dec. 15, 2011

Related U.S. Application Data

(63) Continuation-in-part of application No. 11/609,129, filed on Dec. 11, 2006, now Pat. No. 7,727,511, and a continuation-in-part of application No. 11/609,134, filed on Dec. 11, 2006, now Pat. No. 7,837,981.

(51) Int. Cl.
*A61K 49/00* (2006.01)

(52) U.S. Cl. ......... 424/9.1; 424/1.11; 424/9.5; 424/9.6; 424/1.65; 424/1.81; 436/91; 436/127; 436/128

(58) Field of Classification Search .................... 424/9.1
See application file for complete search history.

(56) References Cited

U.S. PATENT DOCUMENTS

| | | | |
|---|---|---|---|
| 4,716,905 A | 1/1988 | Schmued | |
| 7,837,981 B2 * | 11/2010 | Siclovan et al. | 424/1.69 |
| 2001/0047028 A1 | 11/2001 | Peters et al. | |
| 2003/0232016 A1 | 12/2003 | Heinrich | |
| 2005/0259249 A1 | 11/2005 | Dombeck et al. | |
| 2007/0140960 A1 * | 6/2007 | Siclovan et al. | 424/1.11 |

FOREIGN PATENT DOCUMENTS

| | | |
|---|---|---|
| WO | WO2004087256 | 10/2004 |
| WO | WO2006116634 | 11/2006 |
| WO | WO2007016790 | 2/2007 |
| WO | WO2007028032 | 3/2007 |

OTHER PUBLICATIONS

Keyes et al. J. Nucl. Med. 1995 1836-1839.*
Stankoff et al. Ann Neurol 2011, 673-680.*
Degrand, Alec et al, "An Operational Near-Infrared Fluorescence Imaging System Prototype for Large Animal Surgery", Technology in Cancer Research & Treatment, vol. 2, No. 6, Dec. (2003), pp. 1-10.
Stankoff, B. et al., "Imaging of CNS Myelin by Positron-Emission Tomography", PNAS, vol. 103, No. 24, Jun. 13, 2006, pp. 9304-9309.
Kerschensteiner, M. et al., "Cellular Imaging in the Nervous System", Dtsch Med Wochenschr 2007: 132: pp. 2529-2533.

* cited by examiner

*Primary Examiner* — Michael G Hartley
*Assistant Examiner* — Sean R Donohue
(74) *Attorney, Agent, or Firm* — Eileen W. Gallagher

(57) ABSTRACT

The present invention relates to methods for the detection of myelin and a quantitative measurement of its local concentration in a sample using a benzofuran compound or its radioisotope derivatives. In one embodiment a method of myelin detection comprises identifying a subject at risk of or diagnosed with a myelin-associated neuropathy, parenterally administering to the subject the benzofuran compound, or a derivative of the compound, and determining myelination in the subject by detecting binding in the sample. In one embodiment, the invention provides a method of imaging myelinated tissue in a surgical field of mammalian tissue comprising the steps of contacting the surgical site with the benzofuran compound or a radioisotope derivative of the compound, and detecting binding in the surgical site. In yet another embodiment, a method of imaging spinal cord and spinal nerve root tissue is provided comprising the steps of parenteral administration of a radioisotope derivative of the benzofuran compound and detecting the radioisotope derivative within the spinal canal and intervertebral foramen. Methods of quantification of binding of the benzofuran compound or its derivatives are also provided.

12 Claims, 2 Drawing Sheets

MYELIN DETECTION USING BENZOFURAN DERIVATIVES

CROSS-REFERENCE TO RELATED APPLICATIONS

This application is a continuation-in-part of U.S. patent application Ser. No. 11/609,129 filed Dec. 11, 2006, now issued U.S. Pat. No. 7,727,511, and U.S. patent application Ser. No. 11/609,134 filed Dec. 11, 2006, now issued U.S. Pat. No. 7,837,981.

BACKGROUND

Information flow within the nervous system requires the perpetuation of ionic gradients along neurons. In many neurons, effective and efficient perpetuation of such gradients along axons requires electrical insulation. Myelin, a lipid-rich, dielectric substance that ensheathes axons, serves this insulating function. The nervous system contains high levels of myelin, which is especially enriched where many myelinated axons are bundled together, such as in tracts of the spinal cord and spinal nerve roots, nerves in the peripheral nervous system, and fiber tracts in the brain, collectively called "white matter" (as opposed to "grey matter"). Because non-nervous system tissue lacks myelin, the presence of myelin can distinguish peripheral nerve tissue from other tissue types, the spinal cord and spinal nerve roots from non-nervous elements of the vertebral column, and white matter from grey matter.

The ability to qualitatively or quantitatively visualize myelin, either in vivo or in vitro, confers upon researchers and clinicians important diagnostic and treatment tools. For example, the ability to visually identify peripheral nerves during surgery assists surgeons in avoiding cutting or damaging nerves. Additionally, in vivo myelin imaging of the spinal cord assists clinicians in the diagnosis and treatment of spinal cord pathology, such as nerve compression or herniated discs as well as myelin-associated neuropathies, such as multiple sclerosis which results in damage to myelin within the central or peripheral nervous system. The ability to measure amounts of myelination in vivo in patients with such conditions would aid clinicians and researchers in diagnosing and prognosing myelin-associated neuropathies.

Additionally, myelin detection is useful to preclinical and basic neuroscience researchers. Myelinated nerves and fiber tracts serve as useful landmarks in anatomical studies. Furthermore, the formation of myelin sheaths is an important step in the generation and functional stability of new neurons, so the availability of myelin markers help researchers study such processes. Myelin-labeling methodologies are also useful in the development of numerous therapies, neural stem cell research, and putative animal models of myelin-associated neuropathies.

BRIEF DESCRIPTION

Provided herein are methods for the qualitative or quantitative detection of myelin in an in vitro or in vivo sample using a composition comprising the compound of the following Formula I;

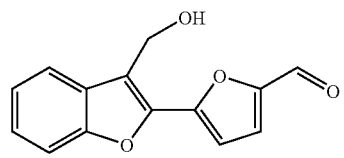

a $^{13}$C or $^{2}$H enriched compound of Formula I, or a radioisotope derivative of Formula I.

In one embodiment, the myelin detection methods may comprise identifying a subject at risk of, or diagnosed with, a myelin-associated neuropathy, by parenterally administering to the subject a composition comprising the compound of Formula I, a $^{13}$C or $^{2}$H enriched compound of Formula I, or a radioisotope derivative of Formula I. Detecting the compound of Formula I, a $^{13}$C or $^{2}$H enriched compound of Formula I, or a radioisotope derivative of Formula I present in the subject may determine myelination in the subject.

In another embodiment, the myelinated tissue is imaged in a surgical field of mammalian tissue comprising the steps of contacting the surgical site with a composition comprising the compound of Formula I or a radioisotope derivative of Formula I, and detecting the compound of Formula I or a radioisotope derivative of Formula I.

In yet another embodiment, the method comprises imaging spinal cord and spinal nerve root tissue by parenterally administering a composition comprising the radioisotope derivative of Formula I, and detecting the radioisotope derivative of Formula I within the spinal canal and intervertebral foramen.

In still another embodiment, the methods of myelin detection comprise contacting a tissue sample from a mammalian subject with a composition comprising the compound of Formula I, a $^{13}$C or $^{2}$H enriched compound of Formula I, or a radioisotope derivative of the compound of Formula I, detecting myelination in the tissue sample by detecting the compound of Formula I, a $^{13}$C or $^{2}$H enriched compound of Formula I, or radioisotope derivative of Formula I present in the sample, and optionally quantifying the amount of the compound present in the sample.

BRIEF DESCRIPTION OF THE FIGURES

These and other features, aspects, and advantages of the present invention will become better understood when the following detailed description is read with reference to the accompanying figures wherein.

DETAILED DESCRIPTION

Figure 1:
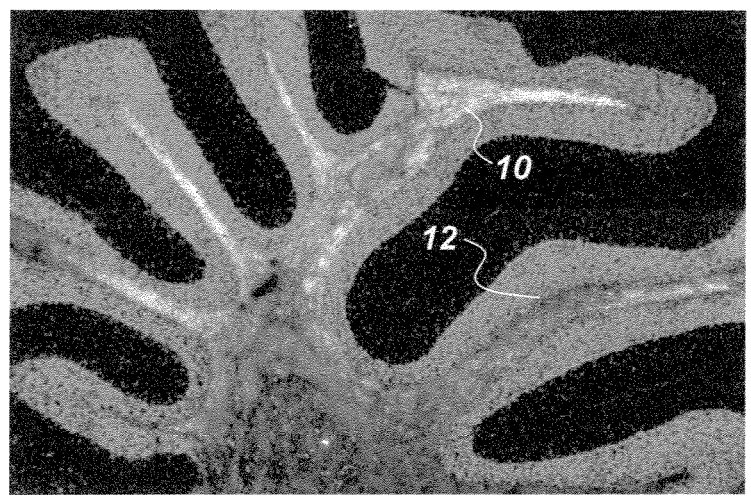
FIG. 1 is a representative image of a rat brain tissue section labeled with the compound of Formula I.

The following detailed description is exemplary and not intended to limit the invention of the application and uses of the invention. Furthermore, there is no intention to be limited by any theory presented in the preceding background of the invention or descriptions of the drawings.

Definitions

To more clearly and concisely describe and point out the subject matter of the claimed invention, the following definitions are provided for specific terms, which are used in the following description and the appended claims.

As used herein, the phrase "myelin-associated neuropathy" generally refers to any condition in which the insulating material ensheathing portions of neuronal cells becomes damaged or dysfunctional as a component of a syndrome, disease, or other pathological condition, such as, but not limited to, multiple sclerosis, Guillain-Barré syndrome, leukodystrophies, metachromatic leukodystrophy, Refsum's disease, adrenoleukodystrophy, Krabbe's disease, phenylketonuria, Canavan disease, Pelizaeus-Merzbacher disease, Alexander's disease, diabetic neuropathy, chemotherapy induced neuropathy, or any combination thereof.

An agent exhibits "specific binding" for myelin if it associates more frequently with, more rapidly with, for a longer duration with, or with greater affinity to, myelin than with tissues not containing myelin. "Non-specific binding" refers to binding of the agent to non-myelin containing tissue. For relative binding values, such as specific binding or non-specific binding, each sample should be measured under similar physical conditions (i.e., temperature, pH, and solvent). Generally, specific binding is characterized by a relatively high affinity of an agent to a receptor and a relatively low to moderate capacity. Typically, binding is considered specific when the affinity constant $K_a$ is at least $10^6$ $M^{-1}$. A higher affinity constant indicates greater affinity, and thus typically greater specificity. For example, antibodies typically bind antigens with an affinity constant in the range of $10^6$ $M^{-1}$ to $10^9$ $M^{-1}$ or higher. "Non-specific" binding usually has a low affinity with a moderate to high capacity. Non-specific binding usually occurs when the affinity constant is below $10^6$ $M^{-1}$. Controlling the time and method used to contact the agent with the tissues reduces non-specific binding.

As used herein, the term "washing" generally refers to any method, such as but not limited to, immersion in, or flushing by repeated application of, a non-labeling solution or other substance, such as but not limited to water, saline, buffered saline, or ethanol, so as to provide a medium for dissociation, dispersal, and removal of unbound or non-specifically bound labeling compound from non-myelinated components of the tissue or sample of tissue without eliminating specific binding to myelin.

As used herein, the phrase "baseline fluorescence" refers to the frequency and magnitude of electromagnetic radiation emitted by a tissue or sample of tissue upon being exposed to an external source of electromagnetic radiation in the absence of administration or binding of any autofluorescing benzofuran compound, as distinguished from the radiation emitted following the administration and binding of such autofluorescing benzofuran compound and exposure to an external source of electromagnetic radiation.

As used herein, the phrase "control sample representative of the tissue section" refers to a tissue sample of a similar size, morphology, or structure as the tissue sample to be analyzed, and with a level of myelin whereby the sample's level of myelin serves as a reference to which other samples' myelin levels may be compared.

The phrase "parenteral administration" refers to any means of introducing a substance or compound into a subject, that does not involve oral ingestion or direct introduction to the gastrointestinal tract, including but not limited to subcutaneous injection, intraperitoneal injection, intramuscular injection, intravenous injection, intrathecal injection, intracerebral injection, intracerebroventricular injection, or intraspinal injection, or any combination thereof.

As used herein, the phrase "demyelination model" refers to any experimentally-induced damage to, or dysfunction of, the insulating material ensheathing portions of neuronal cells, that may be utilized in the experimental study of neuropathic demyelination, including, but not limited to, experimental allergic encephalomyelitis.

The term "remyelination" refers to the spontaneous, therapeutic, or experimentally induced repair, regeneration, or otherwise enhanced constitution or functionality of the insulating material ensheathing neuronal axons.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Imaging Methods

Provided herein are methods for the qualitative or quantitative detection of myelin in a sample utilizing the specific binding to myelin of the compound of Formula I, and its autofluorescence, or the radioactive signal emitted by a radioisotope derivative of the compound of Formula I. In some embodiments, a radioisotope derivative of the compound of Formula I may be used and imaging accomplished through radioimaging. In some embodiments a $^{13}C$ or $^2H$ enriched compound of Formula I may also be prepared. Alternatively, the compound of Formula I without modification may be used and imaged by fluorescence imaging.

Methods applicable in analytical, diagnostic, or prognostic applications related to myelin detection are also included. These may be particularly applicable in intraoperative nerve labeling, spinal imaging, non-invasive in vivo measurement of myelination levels, and preclinical and basic neuroscience bench research aimed at the study of the function and process of myelination, and the dysfunction and repair of myelin.

The compound of Formula I, a $^{13}C$ or $^2H$ enriched compound of Formula I, or a radioisotope derivative of Formula I, may be detected by its emitted signal, such as a magnetic resonance signal or emitted radiation from a radioisotope derivative of Formula I, autofluorescence emission, or optical properties of the agent. The method of detection of the compound of Formula I, a $^{13}C$ or $^2H$ enriched compound of Formula I, or a radioisotope derivative of Formula I, may include fluorescence microscopy, laser-confocal microscopy, cross-polarization microscopy, nuclear scintigraphy, positron emission tomography ("PET"), single photon emission computed tomography ("SPECT"), magnetic resonance imaging ("MRI"), magnetic resonance spectroscopy ("MRS"), computed tomography ("CT"), or a combination thereof, depending on the intended use and the imaging methodology available to the medical or research personnel.

Routes of Surgical Administration

In one embodiment, a composition comprising the compound of Formula I may be administered parenterally to a surgical subject prior to surgery such that the compound of Formula I binds to myelin and may be cleared from tissues that do not contain myelin. In another embodiment, the composition comprising the compound of Formula I may be applied directly to the surgical field during surgery, allowed to bind to myelin present, and the surgical site washed by lavage to clear unbound composition from the site. During surgery, a light source tuned to the spectral excitation characteristics of the compound of Formula I may be applied to the surgical field. The compound of Formula I may be observed through an optical filter tuned to its spectral emission characteristics. Due to their specific binding to the fluorescing compound of Formula I, nerves and other myelin-containing nervous tissue are distinguishable from tissue not containing myelin. This enables the surgeon to avoid inadvertently cutting or damaging myelinated tissue by avoiding fluorescing tissue, or facilitates accurately administering treatment to the intended myelinated tissue.

A composition comprising the compound of Formula I, a $^{13}$C or $^{2}$H enriched compound of Formula I, or a radioisotope derivative of the compound of Formula I, may be administered parenterally to a subject prior to surgery or prior to treatments targeting a nerve or other myelin containing tissue, such as pharmaceutical or surgical nerve block. In one embodiment, a composition comprising the compound of Formula I, or a $^{13}$C or $^{2}$H enriched compound of Formula I, may be administered parenterally to a surgical subject, prior to surgery, to permit binding to myelin, and clearance from tissues that do not contain myelin without the elimination of specific myelin binding. In another embodiment, a composition comprising a radioisotope derivative of the compound of Formula I may be administered parenterally to a subject prior to treatment to permit binding to myelin, and clearance from tissues that do not contain myelin without eliminating specific myelin binding. Imaging techniques such as nuclear scintigraphy, PET, SPECT, CT, MRI, MRS, or any combination thereof, may then be used to aid in differentiation of the myelin and non-myelin containing tissues and may employ a gamma camera, a scanner or a probe.

A composition comprising the compound of Formula I may also be applied directly to the surgical filed during surgery. After binding of the composition to myelin, the surgical site may be washed by lavage to clear unbound compound from the site. During surgery a light source, tuned to the spectral excitation characteristics of the compound of Formula I, may be applied to the surgical field. The surgical field may then be observed through an optical filter tuned to the spectral emission characteristics of the compound of Formula I generating a fluorescence signal. Nerves and other myelin containing tissue, that are bound by the compound of Formula I are distinguished from tissue that do not containing myelin and thus enabling the surgeon to visually identify and pharmaceutically treat or surgically avoid the intended, myelin-containing tissue.

Routes of Non-surgical Administration

In another embodiment, a composition comprising the compound of a radioisotope derivative of Formula I may be administered parenterally to a patient suspected of, or determined to be, suffering from a spinal pathology, such as but not limited to, spinal compression, spinal nerve root compression, or a bulging disc. After binding to spinal myelin, and clearance from tissue that does not contain myelin without eliminating the specific myelin binding, the spine may be imaged for in vivo using radioisotope imaging such as PET, SPECT, or any combination thereof.

By inspection of the diagnostic images, the clinician may determine if, and where, the spinal cord, or associated nerve roots, are impinged, such as by the vertebral column. Additional scans, such as CT or MRI, may also be conducted in conjunction with PET or SPECT scans, to provide additional information, such as the structure and relative positioning of elements of the vertebral column. In one embodiment, this method may be applied to a surgical procedure to image the spinal region intraoperatively.

In another embodiment, myelination level is accessed in vivo by imaging a radioisotope derivative of the compound of Formula I administered parenterally to a subject diagnosed with, or suspected of having, a myelin-associated neuropathy. After binding to myelin, and clearance from tissue that does not contain myelin without eliminating specific myelin binding, components of the central or peripheral nervous system may be imaged by a method suitable for in vivo imaging of the radioisotope, such as PET or SPECT. By inspection of the imaging results, the clinician may determine the amount of myelination, as reflected by levels and anatomical localization of signal emitted by the radioisotope derivative of the compound of Formula I and detected by the appropriate imaging methodology.

To determine whether myelination in the patient may be deficient, myelination levels may be compared to those exhibited by a subject or subjects believed or known not to be suffering from a myelin-associated neuropathy. In another embodiment, rates of demyelination or remyelination may be determined. Following treatment with a known or suggested therapeutic agent believed or anticipated to prevent or slow demyelination or to promote remyelination in patients suffering from myelin-associated neuropathies, myelination levels are evaluated by performing the imaging over time in the patients treated with the therapeutic agent. The imaging may be performed at different points of time and the level of myelination at one time point compared to that of another.

In yet another embodiment, a biopsied mammalian tissue sample, or a tissue sample cultured in vitro, may be contacted with a composition comprising the compound of Formula I, a $^{13}$C or $^{2}$H enriched compound of Formula I, or a radioisotope derivative of the compound of Formula I, to determine the location, presence, or amount of myelin in the tissue sample. The tissue sample may be sampled from a subject that has been experimentally manipulated so as to serve as a verified or purported model of myelin-associated neuropathy, or that has received at least one therapeutic agent verified as, or purported to be, a treatment for myelin-associated neuropathy. The therapeutic agent may be associated with the preclinical evaluation or basic neuroscience research aimed at studying the function and process of myelination, and the dysfunction and repair of myelin.

Fresh frozen cryostatic sections, or fixed or embedded sections or samples, of the biopsy or culture tissue sections, may be contacted with a composition comprising the compound of Formula I, a $^{13}$C or $^{2}$H enriched compound of Formula I, or a radioisotope derivative of the compound of Formula I. The samples may be prepared using various sectioning techniques such as microtome, vibratome, or cryostat preparation After binding to myelin, the sample may be washed in a manner and medium suitable to remove any unbound and non-specifically bound label from the sample, without eliminating specific binding to myelin.

Diagnosing and Prognosing Myelin-associated Neuropathies

Any of a number of detection, visualization, or quantitation techniques, including but not limited to fluorescence microscopy, laser-confocal microscopy, cross-polarization microscopy, autoradiography, MRI, MRS, or other applicable methods, or any combination thereof, may be then be used to assess the presence or quantity of the compound of Formula I, a $^{13}$C or $^{2}$H enriched compound of Formula I, or a radioisotope derivative of the compound of Formula I, in the tissue sample and representing the presence or amount of myelin. The labeling with, and detection, visualization, or quantitation of the compound of Formula I, a $^{13}$C or $^2$H enriched compound of Formula I, or a radioisotope derivative of the compound of Formula I, may also be performed in conjunction with labeling with, and detection, visualization, or quantitation of at least one other compound that specifically binds a substance other than myelin.

EXAMPLES

The following non-limiting Examples are shown and describe various embodiments of the present invention.

Example 1

Synthesis of 2-(2-furanyl-5-formyl)-3-hydroxymethyl benzofuran (Formula I)

Step A: 2-bromo-3-bromomethyl benzofuran 2-bromo-3-bromomethyl benzofuran was prepared using a modified procedure (Helv. Chim. Acta, 1947, 30, 297). To a solution of 3-methylbenzofuran (4 g, 30.26 mmol) in carbon tetrachloride (20 mL), was added benzoyl peroxide (100 mg) and recrystallized N-bromosuccinimide (NBS) (10.8 g, 2 equiv). The mixture was refluxed for 3 h. Product formation was followed by gas chromatography-mass spectroscopy (GC-MS). After analysis, 1.1 g NBS was added and the mixture was refluxed for 1 h followed by a second addition of NBS (1 g, 1 h reflux). The solvent was stripped and replaced with ethanol (12 mL), and the mixture was cooled to −20° C. yielding a mass of yellow crystals, which was filtered at −25° C. The crystals of 2-bromo-3-bromomethyl benzofuran were washed with ethanol (12 mL) at −40° C., filtered, and dried overnight (yield 7.67 g, 87%). Purity as measured by GC-MS was greater than 95%. MS (m/e): 291, 290, 289 (M$^+$), 211, 209, 183, 181, 146, 102, 75.

Step B: 2-bromo-3-hydroxymethyl benzofuran 2-bromo-3-bromomethyl benzofuran prepared from Step A (7.67 g, 26.45 mmol) was immediately dissolved in dioxane (30 mL), followed by a solution of NaHCO$_3$ (2.67 g, 1.2 eq.) in water (30 mL). The mixture was refluxed for 1 h with vigorous stirring, cooled to room temperature, diluted with water (150 mL) and extracted with dichloromethane (5×100 mL). The extract was washed with brine, dried over sodium sulfate, and the solvent removed under reduced pressure. The resulting orange oil was dissolved in chloroform (12 mL) and left to stand at −20° C. The resulting yellow prisms were filtered at −40° C., washed with chloroform, and filtered cold. Yield: 3.72 g (62%). MS (m/e): 228, 226 (M$^+$), 211, 209, 183, 181, 171, 169, 147, 118, 102, 91. $^1$H-NMR (acetone-D$_6$): 4.29 (t, 1H, J=6 Hz) 4.73 (d, 2H, J=6 Hz) 7.32 (m, 2H) 7.51 (d, 1H, J=8 Hz) 7.78 (dd, 1H, J=8 Hz, 2 Hz). $^{13}$C-NMR (acetone-D$_6$): 54.74, 110.64, 119.96, 123.28, 124.57, 126.51, 128.12, 155.37.

Step C: 2-(2-formyl-5-furanyl)-3-hydroxymethyl benzofuran (Formula I)

To the bromo-benzofuran derivative from Step B (0.1 mmol), 2-formylfuran-5-boronic acid (1.5 equiv.), potassium carbonate (1.5 equiv.), palladium dibenzylidene acetone (0.03 eq.) and degassed dimethylacetamide (1 ml) was added. The mixture was blanketed with N$_2$ and heated in a microwave reactor at 120° C. for 10 mins (initial power 50 W). Water (2 mL) was added, the mixture extracted with ether (4×10 mL), the crude extract adsorbed on silica gel, and purified by MPLC (hexanes/ethyl acetate gradient). MS (m/e): 242 (M$^+$), 225, 213, 196, 185, 168, 157, 139, 128, 102, 77. $^1$H-NMR (acetone-D$_6$): 5.15 (s, 2H), 7.19 (d, 1H, J=4 Hz), 7.35 (dd, 1H, J=8 Hz, 1 Hz), 7.44 (dd, 1H, J=8 Hz, 1 Hz), 7.56-7.65 (m, 2H), 7.93 (d, 1H, J=8 Hz), 9.76 (s, 1H). $^{13}$C-NMR (acetone-D$_6$).

Example 2

Synthesis of Formula I Analogs

Synthesis of 2-(2-diaminooxyethenyl-5-furanyl)-3-hydroxymethyl benzofuran (A)

To a solution of Formula I (25 mg, 0.1 mmol) and malononitrile (8.2 mg, 1.25 equiv.) in ethanol (1 mL) was added a catalytic amount of piperidine (0.5 µl, 0.05 equiv). The resulting mixture was stirred at room temperature for 2 h. GC-MS analysis indicated complete conversion to the desired product. The crude mixture was adsorbed on silica gel and flushed through a silica SPE cartridge to give the desired product 99% pure by GC-MS. MS/EI: 290 (100%, M+); 273(50%, M-OH); 261(75%); 246(55%); 233(95%); 206(40%); 177(35%); 151 (38%); 128(40%); 89(60%).

Synthesis of 2-(2-diaminooxyethenyl-5-furanyl)-3-ethylacetyl benzofuran (B)

To a solution of 2-(5-formyl-2-furyl)-3-(acetoxymethyl) benzofuran (57 mg, 0.2 mmol) and malononitrile (16.5 mg, 1.25 equiv.) in 2 mL ethanol and 0.25 ml ethyl acetate was added a catalytic amount of piperidine (1 µL, 0.05 equiv.). The resulting mixture was stirred at room temperature for 2 h. The crude mixture was adsorbed on silica gel and flushed through a silica SPE cartridge to give the desired product 99% pure by GC-MS. MS/EI: 332 (80%, M+); 290 (100%, M-CH$_2$CO); 273 (90%, M-CH$_3$CO$_2$); 262(50%); 245 (80%); 238(40%); 190(70%); 139(75%).

Example 3

Radiolabeling of Formula

Step A: [$^3$H]2-bromo-3-hydroxymethyl benzofuran

To aldehyde 2-bromo-3-formyl-benzofuran (15 mg, 66 µmol) in propan-2-ol: water (600 µL of a 4:1 solution) was added a solution of NaBT$_4$ (5 Ci at approx. 56 Ci/mmol) in propan-2-ol: water (600 µl of a 4:1 solution). The resulting mixture was stirred at room temperature for 2 h. The residue was dissolved in ethyl acetate (5 mL) and a sample analyzed by silica TLC eluting in dichloromethane:methanol (95:5). Yield: 15 Ci/mmol, 260 mCi (17 µmol).

Step B: [$^3$H]2-bromo-3-acetoxymethyl benzofuran

Three equivalents of acetic anhydride (5 µL) were added to 17 µmol of [$^3$H]2-bromo-3-hydroxymethyl benzofuran. TLC monitored the acetylation. After 2 h, an additional 10 µL of acetic anhydride was added and the mixture was swirled and left overnight. After a total of 18 h the reaction preceded approximately 50%. A further 50 µL of acetic anhydride was added and the mixture was left for an additional 2 h. An additional 50 µL of acetic anhydride was added and the reaction mixture was left for a second night, after which the reaction appeared to have progressed to near completion. The crude mixture was purified by HPLC using an Ultrasphere (Beckman Coulter) ODS column eluting with a 0.1% TFA in a water/acetonitrile gradient. A rotary evaporated was used to dry the [³H]2-bromo-3-acetoxymethyl benzofuran fractions.

Step C: [³H] Labelled Formula I

To [³H]2-bromo-3-acetoxymethyl benzofuran (100 mCi) was added K$_2$CO$_3$ (1.4 mg), 5-formyl-furan-2-boronic acid (1.4 mg), [Pd2dba3] (0.2 mg), and degassed dimethylacetamide (400 μL). The mixture was blanketed under nitrogen gas and heated with stirring at 80° C. for 6 h. The reaction mixture was analyzed by TLC silica eluting in CH$_2$Cl$_2$:MeOH (95:5).

Deacetylation was performed by adding sodium hydroxide, 0.5 mg in THF:methanol (1:1), to the mixture. The reaction was swirled and stirred at room temperature. Samples were periodically analyzed by TLC and after 3 h the reaction mixture was rotary evaporated to a lower volume and applied to a 2 g Sep-Pak cartridge. The required fraction was counted, analyzed and purified by HPLC using an Ultrasphere C18 column eluting with a water/methanol gradient, followed by another purification by HPLC using an Ultrasphere C18 column eluting with a water/acetonitrile gradient. The final product was analyzed by HPLC and mass spectrometry. Yield: specific activity of 13 Ci/mmol and 96.7% radiochemical purity.

Example 4

Measurement of Fluorescence Properties and Solubility of benzofuran Compositions Fluorescence excitation and emission peaks for Formula I, and benzofuran compounds A and B, (see Table 1) were measured using a Spetramax M5 (Molecular Devices). For Formula I, the excitation max was 380 nm, and the emission max was 470 nm. For compound A, the excitation max was 435 nm and the emission max was 550 nm. For compound B, the excitation max was 435 nm and the emission max was 535 nm. The final concentration of each analog in an aqueous solution was 10 μM. Log P, which is the logarithm of octanol-water partition coefficient, was determined for each analog using commercially available software (Table 1). The log D value for Formula I, which is its log P value at pH 7.4, was 1.3, indicating its ability to penetrate the lipid membranes. For compound A and B, the log D values were 2.2 and 2.6, respectively, indicating reduced penetrability.

TABLE 1

| Benzofuran Compound | Excitation max (nm) | Emission max (nm) | Log D (Log P at pH 7.4) |
|---|---|---|---|
| Formula I | 380 | 470 | 1.3 |
| A | 435 | 550 | 2.2 |

TABLE 1-continued

| Benzofuran Compound | Excitation max (nm) | Emission max (nm) | Log D (Log P at pH 7.4) |
|---|---|---|---|
| B | 435 | 535 | 2.6 |

Example 5

Staining of Cryostatic Sections of Nervous Tissue

10 μm-thick sections (fresh frozen or formalin-fixed) of rat brain and cross-sections of sciatic, optic, and penile nerves were mounted on microscope slides, washed 3×5 min in phosphate buffered saline (PBS), then drained for 2 min. 1 mM stock solution of Formula I was prepared in 50% ethanol and 50% deionized water. The solution was vortexed and centrifuged at 10,000×g, and the supernatant, containing fully dissolved Formula I was transferred into a fresh tube. The solution was diluted to 25 uM in 50% ethanol. 200 uL of the 25 uM Formula I was pipetted onto the microscope slides. Control sections were treated with 50% ethanol. Parafilm was placed over sections during 10 min incubation at room temperature. Unbound compound was rinsed by serial immersion in 3×1 min washes in 50% ethanol, followed by a 1 min wash in de-ionized, distilled water. For cell body counterstaining, sections were immersed in 100 uL of 500 nM propidium iodide (PI) in PBS and carefully covered with parafilm. The sections were incubated for 5 min at room temperature. The samples were repeatedly rinsed and washed with PBS (3×10 min), followed by de-ionized, distilled water. The sections were covered with 20 uL of AntiFade Gold (Molecular Probes Inc, Carlsbad Calif.) and examined microscopically. Images were collected on a Leica DMRA2 fluorescent microscope equipped with filter cubes for near ultraviolet and visible fluorophores. Fluorescence was visualized using a Leica "A" filter cube while PI was imaged with a Leica "TX2" cube.

Staining of sciatic nerve sections by Formula I was also compared to a commercially available myelin stain (Fluoro-Myelin, Invitrogen). The tissue sections were dehydrated by incubating in PBS for 5 minutes, followed by permeabilized with PBS containing 0.2% Triton X-100 for 20 minutes. The staining solution was prepared by 300-fold dilution of a stock solution of DAPI and a stock solution of Fluoromyelin green fluorescent myelin. Each section was flooded with 100 uL of the staining solution, covered with a small piece of parafilm and allowed to incubate for 20 min. The parafilm was removed and all sections were washed 3×5 min in PBS and rinsed with de-ionized, distilled water. After drying, the tissue sections were covered with 20 uL of AntiFade Gold (Molecular Probes Inc) and examined microscopically.

FIG. 1 is an image of a rat brain tissue section labeling with the compound of Formula I. Formula I labeling is concentrated in the lighter, centrally located portion of the sample (10), and resembles the distinctive myelin-rich white matter in this region of the brain (cerebellum). The outer periphery (12), which surrounds the white matter and is comparatively enriched in nonmyelinated grey matter, shows concentrated labeling with the counter stain PI. The image demonstrates the compound of Formula I's specific labeling of myelin.

Similarly, the compound of Formula I labeling of sectioned peripheral nerves showed the distinctive rings of labeling indicative of cross sections of myelin ensheathing unlabeled axon shafts, as also shown with the myelin stain FluoroMyelin. In contrast, the fluorophoric Formula I analogs benzofuran A and B did not label brain or nerve tissue above background autofluorescence.

Example 6

Staining of Explanted Nerves

Freshly explanted sciatic nerve was incubated in Formula I then imaged under an ultraviolet transilluminator to visualize myelin. Rats were euthanized and within 30 min, 2 cm-long segments of their sciatic nerve tissue were collected, rinsed with PBS, then washed 3×5 min in 50% ethanol. The nerves were incubated at RT in the dark for 20 min in a solution of Formula I as prepared in Example 1. Control nerves were incubated in 50% ethanol. Nerves were rinsed 3×3 min in 50% ethanol, followed by de-ionized distilled water, and mounted on glass slides. Samples were placed on a transilluminator (long wavelength, ≧350 nm) and photographed. Sciatic nerves treated with Formula I showed distinctive fluorescence over background, whereas control-treated sections did not fluoresce above background.

Example 7

Kinetics and Biodistribution of Formula I

100 µl of [$^3$H] labeled Formula I, diluted in saline to 740 kBq/ml, was injected into the tail vein of female mice weighing 18+/−g. Mice were killed by $CO_2$ at 2, 5, 15, 30, or 60 min post-injection and organs immediately dissected out. Organs were weighed, transferred to scintillation tubes containing 2 ml Biolute-S (Zinsser Analytic GmbH, Germany), and tubes were shaken overnight at room temperature. Subsequently, 200 µL of glacial acetic acid was added and after 1 h, 10 mL of scintillation fluid was added (Ready Organics, Beckman Coulter). The tubes were shaken vigorously, allowed to rest for 1 h, and radioactivity was measured in scintillation counter (LS 6000LL, Beckman Instruments). Blood, also sampled at each time point, was collected in heparinized tubes. 10 µL of each sample was added to 2 ml Biolute-S. A similar procedure was used for the other organs studied.

Biodistribution of Formula I at different time points following administration was expressed as standard uptake values (SUVs), according to the following formula wherein RA is a measure of radioactivity:

$$SUV = \frac{RA(\text{organ}) \times \text{Weight (animal)}}{RA(\text{injected}) \times \text{Weight (organ)}}$$

Figure 2:
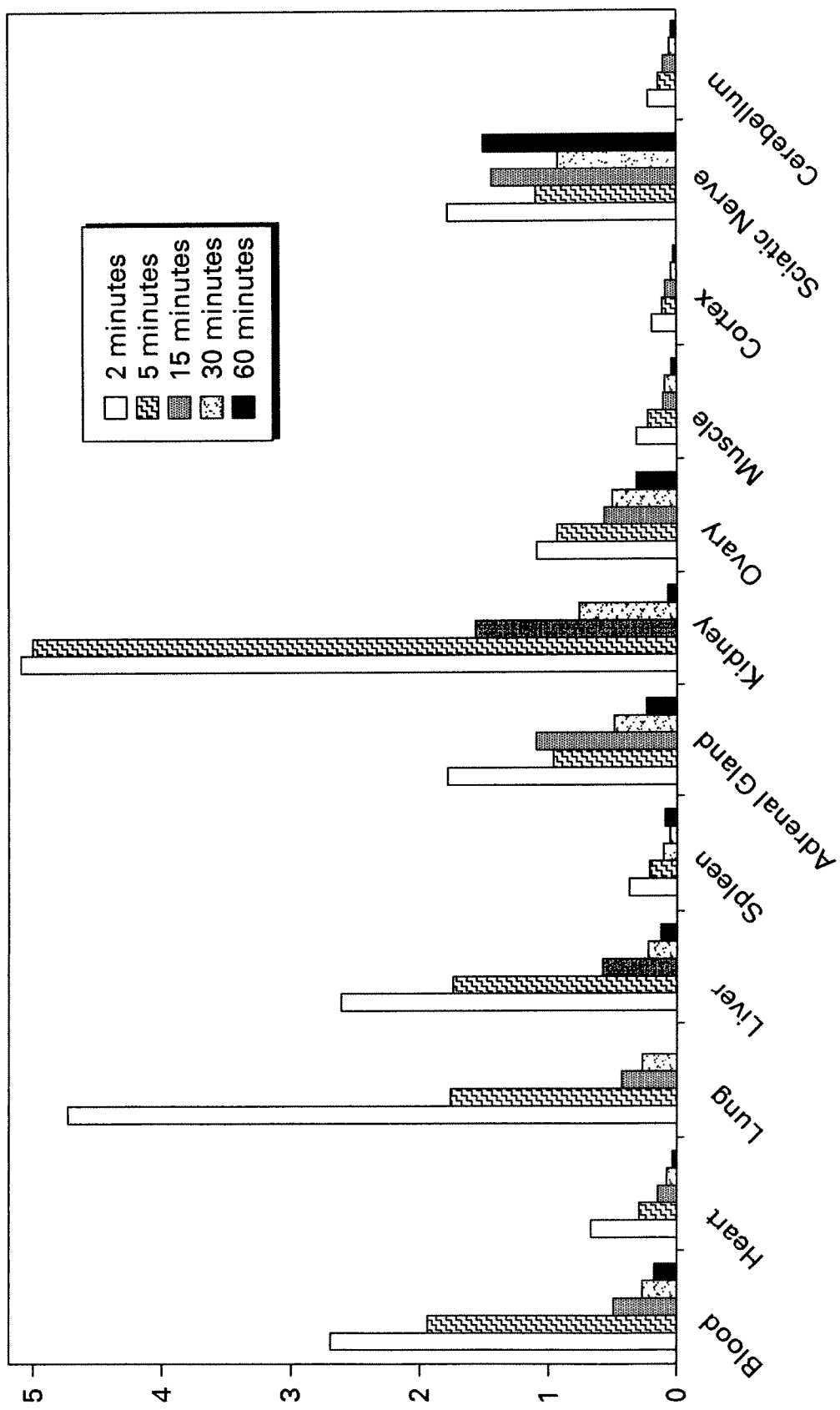
FIG. 2 shows standard uptake values (SUV) of radiolabel Formula I in various bodily tissues at 2, 5, 15, 30, and 60 minutes after systemic injection.

FIG. 2 shows SUV of [$^3$H] labeled Formula I in various bodily tissues at 2, 5, 15, 30, and 60 min after systemic injection. Non-myelinated tissues showed an initial, brief increase in radioactivity uptake following [$^3$H] labeled Formula I administration, which rapidly subsided. In notable contrast is the myelin-rich sciatic nerve, which retained radioactive signal long after non-specific uptake in other tissue types had dissipated. Also, there is a marked absence of uptake in myelin-rich cortex and cerebellum following peripheral administration, indicating that [$^3$H] labeled Formula I was unable to cross the blood-brain barrier to enter the brain from the bloodstream.

Figure 3:
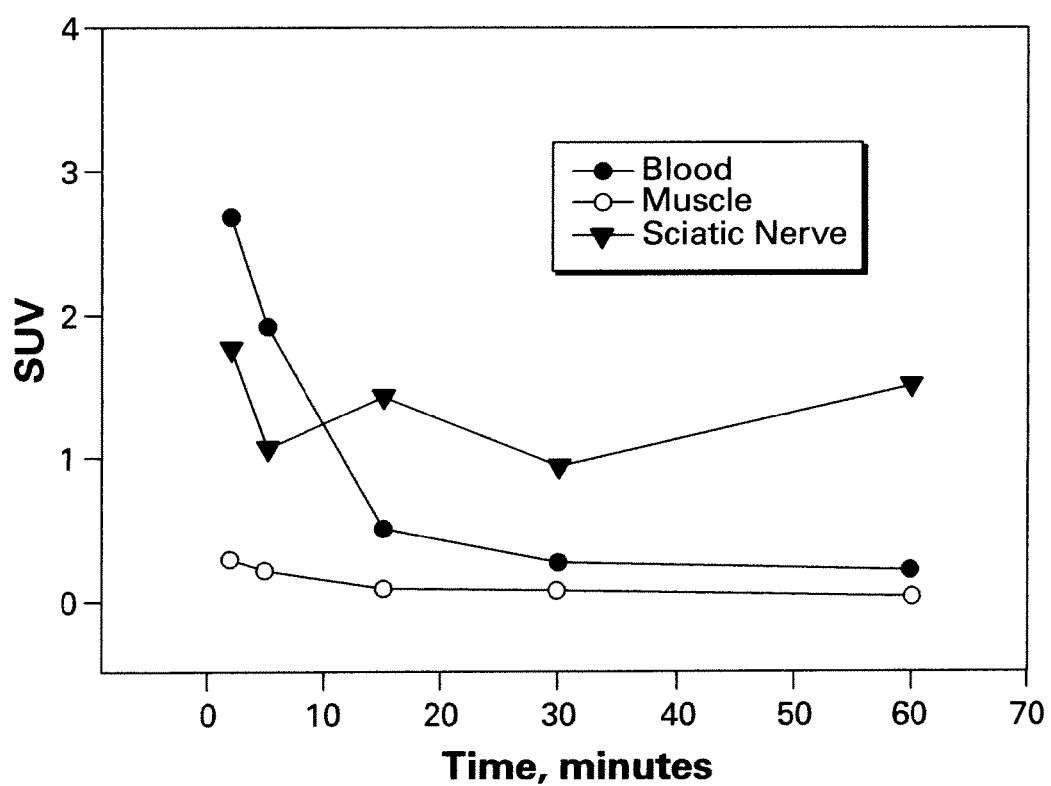
FIG. 3 shows a comparison between standard uptake values (SUV) of radiolabeled Formula I in blood, muscle, and sciatic nerve at various times after systemic injection.

Direct comparisons between the SUV across time of blood, muscle, and sciatic nerve are presented in FIG. 3. Multiple tissues showed a rapid, transient peak in SUV that declined to baseline levels within 60 min. SUV of myelin-rich sciatic nerve, by comparison, remained elevated throughout the sampling period. SUV of richly myelinated brain regions, cortex and cerebellum, were low at all time points, with SUV <0.2 at 2 min post-injection, indicating that Formula I does not readily penetrate the blood-brain barrier.

As shown further in FIG. 3, the persistent radioactive retention by the sciatic nerve, far above absorption by muscle tissue and long after its clearance from the blood stream, signifies Formula I's affinity for and specific binding to myelin.

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

The invention claimed is:

1. A method of myelin detection comprising:
 contacting a tissue sample from a mammalian subject with a compound of Formula I, a $^{13}$C or $^2$H enriched compound of Formula I, or a radioisotope derivative of the compound of Formula I;

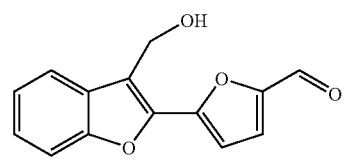

detecting myelination in the tissue sample by detecting the compound of Formula I or radioisotope derivative of Formula I present in the sample; and
 optionally quantifying the amount of the compound of Formula I, a $^{13}$C or $^2$H enriched compound of Formula I, or radioisotope derivative of Formula I present in the sample.

2. The method of claim 1 wherein the mammalian subject constitutes a verified or putative animal model of myelin-associated neuropathy.

3. The method of claim 1 wherein the tissue sample comprises biopsied or explanted tissue.

4. The method of claim 1 wherein the tissue sample comprises tissue grown in culture.

5. The method of claim 1 wherein the detecting is effected by fluorescence microscopy, laser-confocal microscopy, cross-polarization microscopy, autoradiography, magnetic resonance imaging, magnetic resonance spectroscopy, or combination thereof.

6. The method of claim 1 wherein the quantifying step comprises:
 (a) measuring at least one baseline fluorescence emission peak of the tissue sample;
 (b) measuring at least one fluorescence emission peak of the tissue section after contact with the compound of Formula I; and
 (c) calculating the amount of binding using the measurements of (a) and (b).

7. The method of claim 6 wherein measuring at least one fluorescence emission peak comprises measuring fluorescence of the tissue section prior to contacting with the compound of Formula I or measuring fluorescence of a control sample representative of the tissue section.

8. The method of claim 1 wherein the contacting step comprises parenteral administration of the radioactive derivative of Formula I.

9. The method of claim 8 wherein the quantifying step comprises:
   measuring the radioactivity of the parenteral;
   measuring the radioactivity of the tissue sample;
   measuring the weight of the tissue sample; and
   calculating the percentage of radioactivity of the parenteral per gram of tissue.

10. The method of claim 9 further comprising measuring the weight of the subject and calculating standard uptake value (SUV).

11. The method of claim 1 wherein the contacting step further comprises dissolving or suspending the compound of Formula I, a $^{13}$C or $^{2}$H enriched compound of Formula I, or a radioisotope derivative of Formula I in a polar solution prior to contacting with the tissue sample.

12. The method of claim 10 wherein the polar solution further comprises reagents to make the solution an acceptable pharmaceutical carrier.

* * * * *